(12) United States Patent
Popescu

(10) Patent No.: US 7,043,114 B2
(45) Date of Patent: May 9, 2006

(54) APPARATUS TO TRANSFER OPTICAL SIGNALS BETWEEN A ROTATING PART AND A STATIONARY PART OF A MACHINE

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 100 days.

(21) Appl. No.: 10/886,342

(22) Filed: Jul. 7, 2004

(65) Prior Publication Data

US 2005/0013535 A1 Jan. 20, 2005

(30) Foreign Application Priority Data

Jul. 7, 2003 (DE) ................. 103 30 647

(51) Int. Cl.
G02B 6/26 (2006.01)
G02B 6/32 (2006.01)
H04B 10/00 (2006.01)

(52) U.S. Cl. .................. 385/26; 385/27; 385/33; 385/50; 385/51; 398/116

(58) Field of Classification Search ............ 385/25–27, 385/33, 50, 51; 398/116
See application file for complete search history.

(56) References Cited

U.S. PATENT DOCUMENTS 3,746,454 A 7/1973 Pace et al.
4,259,584 A 3/1981 Krumme
4,555,631 A 11/1985 Martens (Continued)

FOREIGN PATENT DOCUMENTS

DE 44 21 616 C2 3/1995

OTHER PUBLICATIONS

Oliver Graydon, ,,Optical antenna enhances IR links, Opto & Laser, Europe, Dec. 2002, Issue 101, p. 9.

(Continued)

Primary Examiner—Frank G. Font
Assistant Examiner—Michael P. Mooney
(74) Attorney, Agent, or Firm—Schiff Hardin LLP

(57) ABSTRACT

The present invention concerns an apparatus for transmission of optical signals between a rotating part and a stationary part of a machine, particularly a computer tomograph, in which an optical transmitter is arranged on a first of the two parts and an optical receiver with an optical detector is arranged on a second of the two parts, via which optical signals emitted by the optical transmitter are received, whereby the optical receiver comprises an optical concentrator with an at least approximately horn-shaped geometry that concentrates incident optical radiation via internal reflection on side surfaces of the concentrator onto a detection area of the detector. The optical concentrator is formed from a material filling the entire inner volume of the concentrator and optically transparent for at least one wavelength with which the transmitter transmits. A signal-to-noise ratio improved relative to that of known apparatuses for data transmission can be achieved with the present apparatus.

9 Claims, 3 Drawing Sheets

U.S. PATENT DOCUMENTS

| | | |
|---|---|---|
| 4,898,450 A | 2/1990 | Jannson et al. |
| 4,996,435 A | 2/1991 | Keller |
| 5,134,639 A | 7/1992 | Vekstein et al. |
| 5,229,871 A | 7/1993 | Czarnek et al. |
| 5,469,488 A | 11/1995 | Ono |
| 5,535,033 A | 7/1996 | Guempelein et al. |
| 5,847,835 A | 12/1998 | Fukunaga |
| 6,043,916 A | 3/2000 | Poisel et al. |
| 6,396,613 B1 | 5/2002 | Harrison et al. |
| 6,937,787 B1 * | 8/2005 | Schilling et al. ............... 385/26 |
| 2002/0081760 A1 | 6/2002 | Whatmore |
| 2004/0062344 A1 * | 4/2004 | Popescu et al. ............... 378/15 |

OTHER PUBLICATIONS

Femto second pulses generate microstructures, Opto & Laser Europe, Dec. 2002, Issue 101, pp. 22-23.

Oliver Graydon, ,,A plastic lens with a high light-collecting efficiency could revolutionize infrared "point-and-pay schemes", OLE, 13. Dec. 2002.

* cited by examiner

APPARATUS TO TRANSFER OPTICAL SIGNALS BETWEEN A ROTATING PART AND A STATIONARY PART OF A MACHINE

BACKGROUND OF THE INVENTION

The present invention concerns an apparatus to transfer optical signals between a rotating part and a stationary part of a machine, particularly a computer tomograph in which an optical transmitter is arranged on a first of the two parts and an optical receiver with an optical detector is arranged on a second of the two parts, via which optical signals emitted by the optical transmitter are received. The optical receiver comprises an optical concentrator with an at least approximately horn-shaped geometry that concentrates incident optical radiation via internal reflection on side surfaces of the concentrator onto a detection area of the detector.

In many fields of technology today large data quantities are transferred between elements moving relative to on another at a slight distance, particularly individual apparatus parts of a measurement apparatus. The data are thereby frequently acquired with an adjustable apparatus part and, for further processing, must be transmitted during the data acquisition to an evaluation device on a stationary apparatus part. Examples of such an application include medical imaging, and particularly computer tomography, in which a large quantity of measurement data must be transmitted from a rotating part (what is known as the gantry) to the stationary part in real time during the rotation. The available transmission rate represents an important criterion for the data quantity that can be transmitted in real time.

In a computer tomograph, the measurement data are acquired via x-ray detectors attached to the gantry opposite an x-ray source and transmitted to the stationary part within which the gantry rotates during the measurement. The transmitted measurement data are then further processed for reconstruction of slice images of the examined body and shown to the operator. The data transmission between the rotating part and the stationary part normally ensues using a "data transmission ring", which is concentrically mounted around the rotation axis, either on the stationary part or on the rotating part, and which during the rotation exhibits a slight separation from a transmitter or receiver attached on the opposite part. The measurement data are thereby transported via the data transmission ring. The coupling between the data transmission ring and the transmitter or receiver mounted on the part lying opposite is in many cases realized as a radio-frequency connection via capacitively coupled antennas.

Newer generations of computer tomographs are in the position to simultaneously acquire a plurality of slices of the examined body, such that much larger data quantities per time unit must be transferred by the increasing number of measurement channels for each additional slice. For particular applications such as with newer developments in heart computer tomography, the rotation speed of the gantry must be increased, resulting in the number of the data to be transmitted per time unit increasing.

For example, a known multi-slice computer tomography that simultaneously records at a rotation speed of 140 revolutions/min requires a data connection with a capacity of approximately 800 Mbaud. Via a further increase of the number of simultaneously acquired layers as well as of the rotation speed, transfer rates of up to in the range of 2.5–10 Gbaud can be achieved. With known radio-frequency transmission techniques, the data transmission with such a high transmission rate is problematic since the distance between the rotating part and the stationary part is comparable to a quarter of the wavelength. Shorter wavelengths lead to an increase of the costs for the maintenance of the mechanical precision and the adjustment of the individual components of the system. Furthermore, it becomes increasingly more difficult to deal with problems of the electromagnetic compatibility. For high transfer rates in computer tomographs, optical signal transmission techniques are therefore increasingly used. The presently known optical transmission techniques can be divided into four different concepts that are briefly explained in the following.

U.S. Pat. Nos. 4,996,435, 5,229,871 ("the '871 Patent") and U.S. Pat. No. 5,469,488 ("the '488 Patent") specify transmission systems in which the transmitter comprises a plurality of light sources that are attached to the rotating part. The light sources generate overlapping light rays modulated with the measurement data, these light rays being received by one or more detectors of the receiver on the stationary part.

To increase the light yield, in the '871 Patent, elliptical reflectors with a single or double curve are used that deflect the incident optical radiation onto the detectors. In the '488 Patent, the use of an optical concentrator is specified that concentrates the incident optical radiation onto a detection area of the detector via internal reflection on side surfaces. The concentrator exhibits an approximately horn-shaped geometry with planar side surfaces that are formed via metallically-coated resin plates. However, the production precision of such a concentrator is insufficient for many applications with higher transmission rates. The transmission technique used in these printed publications is additionally only applicable for low data rates, since the adaptation of the electrical delay between the many feed lines that lead to the light sources and/or receivers is difficult.

In a second known optical transmission technique, such as that known from, for example, German Patent Document DE 4421616 C2 or U.S. Pat. No. 6,043,916 ("the '916 Patent"), the modulated light of a light source arranged on a rotating part is laterally coupled into a ring of an optical fiber concentrically attached to the rotation axis on the stationary part. The light propagating in the fiber is received by a detector coupled at the axial end of the fiber.

The greatest difficulty in the realization of this technique exists in the lateral coupling of light into the fiber core with sufficient efficiency. Different solutions are proposed for this. In the case of the '916 Patent, a special fluorescent fiber material is used that is excited by the optical radiation emitted by the transmitter; the receiver detects the excited fluorescent radiation.

A second known possibility exists in the use of a specially produced synthetic fiber with small entrance windows into the fiber cladding which enable the lateral light entrance directly into the fiber core. The lateral light coupling efficiency is very good in this case. However, the entrance windows cause a very severe damping of the coupled light upon the propagation in the fiber. A problem common to both techniques exists in the coupling of the axially modulated light (escaping from the fiber) in the photodetector, which normally exhibits a smaller detector area than the exit area of the fiber core.

In a further known signal transmission technology such as is used, for example, in U.S. Pat. Nos. 5,535,033, 4,259,584 and 6,396,613, the light modulated with the signals is axially coupled at the rotating part into an optical fiber that is attached annularly and concentrically (relative to the rotation axis) to the rotating part. The optical fiber comprises a transparent fiber cladding and is thus modified such that it also laterally radiates the coupled light. A receiver arranged on the stationary part detects the light emitted by the fiber ring. The coupling efficiency for the coupling of the modulated light in the fiber is very good. However, the lateral emission effects a severe weakening of the signal along the fiber.

Different techniques are used to generate the lateral emission. In one technique, a synthetic fiber with a partially uncovered core is used, in another technique a synthetic fiber with integrated bubbles is used via which the light is laterally scattered. Due to the high losses of this transmission technique in which, respectively, light is emitted over the entire length of the fiber ring but is detected only at one location at which the receiver is directly located, the optical receiver must possess a high dynamic range as well as a large detection angle in order to improve the signal-to-noise ratio via the detection of an optimally large portion of the emitted light.

In a further known optical signal transmission technique, the stationary part and the part rotating at a slight distance from the stationary part are fashioned such that a light-reflecting, hollow light channel is formed on the inner surfaces between both parts. The light can thereby be coupled by the rotating part into the light channel and decoupled from the light channel at the stationary part. Different embodiments for the realization of this transmission technique are, for example, known from U.S. Pat. Nos. 4,555,631, 5,134,639, and U.S. patent Publication 2004/0062344.

In one of the known embodiments, the hollow light channel is formed by a first half that rotates with the gantry and a second half that is arranged on the stator of the gantry. In this embodiment, the light exiting from the light channel exhibits a high dispersion, due to mechanical tolerances and irregularities of the reflecting surfaces. Here as well, the photodetector must possess a large incident angle range and a large detection area in order to achieve a sufficient signal-to-noise ratio.

All previously known transmission techniques to transmit optical signals between a rotating part and a stationary part of a machine require an optimally efficient collection of the dispersed and scattered light for the consolidation on the small detection area of the receiver used. The use of microlenses is in many cases unsuited for this, since these are not in the position to focus incident light onto the receiver in different directions and with different propagation modes. Moreover, the effect of the mode hopping that occurs given the lasers used most in this field reduces the efficiency of the focusing of a lens.

The use of an optical detector with a large detection area does in fact enlarge the quantity of light that can be acquired, however leads to a loss in bandwidth. Furthermore, detectors with a large detection area are severely limited in terms of the maximum processable data rate. Thus, for example, an avalanche photodiode (APD) can only process up to approximately 1 Gbps. The cause for the limitation of the processable data rate lies primarily in parasitic electrical capacities of the photosensitive region that are proportional to the detection area. To increase the processable data rate, detectors with smaller detection areas must therefore be used that, however, in turn capture only a reduced light quantity.

SUMMARY OF THE INVENTION

Starting from this prior art, the object of the present invention is to provide an apparatus for transmitting optical signals between a rotating part and a stationary part of a machine that enables a higher signal-to-noise ratio relative to the known apparatuses.

The object is achieved with an apparatus for transmission of optical signals between a rotating part and a stationary part of a machine, comprising: an optical transmitter arranged on a first of the two parts; an optical receiver with an optical detector arranged on a second of the two parts, via which optical signals emitted by the optical transmitter are received, the optical receiver comprising: an optical concentrator with an at least approximately horn-shaped geometry for concentrating incident optical radiation via internal reflection on side surfaces of the concentrator onto a detection area of the detector, the optical concentrator being formed from a material filling an entire inner volume of the concentrator and optically transparent for at least one wavelength with which the transmitter transmits, the material being capable of being generated via two-photon polymerization.

The present apparatus, which is particularly suited for transmitting optical signals between the rotating part and the stationary part of a computer tomograph, comprises an optical transmitter at the first of the two parts and an optical detection device with optical detector at the second of the two parts, via which the optical signals emitted by the optical transmitter are received.

The transmitter is thereby normally arranged on the rotating part; however, as necessary, it can also be attached to the stationary part. The optical receiver comprises an optical concentrator with an at least approximately horn-shaped geometry that concentrates the incident optical radiation onto a detection area of the detector via internal reflection on its side surfaces.

The present apparatus characterizes itself in that the optical concentrator is formed from a material filling the entire internal volume of the concentrator and optically transparent for at least one wavelength with which the transmitter transmits. The horn-shaped geometry can be selected as with horn antennas known from radio-frequency technology. However, the side surfaces of the concentrator preferably do not run in a straight line from the exit area to the entrance area, but rather are internally curved, such that the diameter of the concentrator non-linearly increases from the exit area to the entrance area.

The further embodiment of the present apparatus, particularly the design and arrangement of the transmitter and/or a possibly used data transmission ring can thereby be selected in a known manner. Thus all of the embodiments of optical signal transmission systems listed above can be equipped with the present optical concentrator.

A significant feature of the present apparatus exists in the design of the optical concentrator with an approximately horn-shaped geometry, made from a transparent material that can be manufactured with high precision and that completely fills the inner volume of the concentrator. A larger spatial angular portion of the scattered light is captured by the horn-shaped geometry and concentrated via internal reflections onto the small area of the optical detector. The geometry, in particular of the side surfaces of this concentrator, can be mathematically predicted (and thereby optimized) for different gathering angles and different optical acquisition.

The geometric design of this concentrator is preferably selected dependent on concentrators as they are used to maximize the collector efficiency in solar cells. Such optical concentrators are, for example, known from Oliver Graydon, "Optical antenna enhances IR links", Opto & Laser Europe, December 2002, Issue 101, page 9. Also proposed in this publication is a use of these concentrators for short-range infrared transmission in television apparatuses, mobile telephones, PDAs, laptop computers and in automatic payment systems, for example on highways.

The presently used concentrator is formed from a fill material that is transparent at least in the wavelength range used for the signal transmission and comprises, on a convexly-fashioned entrance area, an anti-reflection coating for this wavelength range as well as a coating on the side surfaces increasing the internal reflection of these wavelengths. Furthermore, the concentrator body can be provided with a bandpass coating on the exit area directed towards the detector, said bandpass coating being permeable for the wavelengths used and impermeable for longer wavelengths. The dimensioning and the use of anti-reflection coatings, high-reflection coatings and coatings to generate a multi-layer bandpass filter are known to one of ordinary skill in the art.

The present application in the transmission of optical signals between a rotating part and a stationary part of a computer tomograph does not enable the use of the concentrators known from O. Graydon, which are produced from polymers via injection molding. These concentrators do not fulfill the requirements of the present application, in which a precision of a few micrometers is necessary. The present concentrator is therefore preferably formed from an organically modified ceramic material, in particular an Ormocer® as it is known from publications by the Frauenhofer Institute for silicate research. This hybrid polymer enables the adjustment of a refraction index in the range of 1.47–1.56, exhibits losses of less than 0.06 dB/cm at a wavelength of 830 nm, and exhibits an extraordinarily good thermal and mechanical stability with low production costs. The material enables in particular a production of the concentrator with a two-photon polymerization process such as it is, for example, known from "Femtosecond pulses generate microstructures", Opto & Laser Europe, December 2002, Issue 101, pages 22–23. With this production process, the concentrator can be manufactured with a precision of 100 to 200 nm.

In the present apparatus, a photodiode with a detector area with a diameter of $\leq 0.5$ mm is preferably used as a detector. The optical concentrator is thereby fashioned such that it concentrates the captured light onto this small region.

DESCRIPTION OF THE DRAWINGS

The present apparatus is subsequently briefly explained using exemplary embodiments in connection with the drawings.

DETAILED DESCRIPTION OF THE PREFERRED EMBODIMENTS

Figure 1:
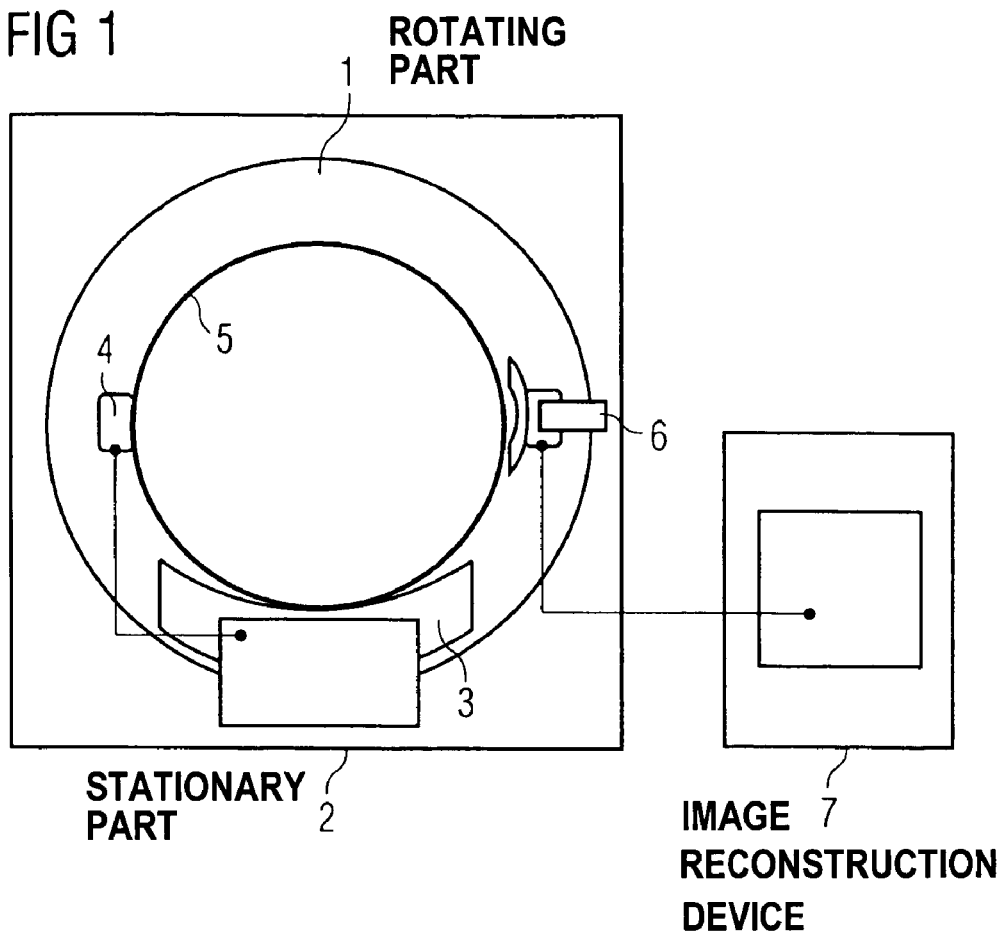
FIG. 1 is a block schematic diagram illustrating an arrangement utilizing the signal path of the measurement data in an exemplary computer tomograph.

FIG. 1 shows an embodiment of the transmission path of the measurement data in a computer tomograph that is shown only in a substantially schematic manner without the x-ray source. The measurement data are thereby acquired by the detector bank 3 arranged on the rotating part 1 and transmitted to the transmitter 4 after a parallel-serial conversion. The transmitter 4 comprises a data transmission ring 5 in which the signals propagate. On the stationary part 2, a receiver 6 is arranged that, during the rotation, receives signals decoupled from the ring 5 and forwards them to an image reconstruction device 7 in which the data are extracted from the transmitted signals and undergo a serial-parallel conversion before the further processing. The reception part of the receiver 6 is hereby arranged in direct proximity to the data transmission ring 5 in order to increase the efficiency of the data transmission between both of the elements during the rotation.

While previously common radio-frequency transmission techniques have been used for transmission between the rotating part 1 and the stationary part 2, with increasingly larger data quantities, optical transmission techniques (as they have previously been explained above) are used. The data transmission ring 5, arranged concentric to the rotation axis, is normally fashioned from an optical wave guide or an optical fiber in which the optical transmitter 4 couples light modulated with the measurement data. The receiver 6 comprises an optical detector, particularly a photodetector.

Figure 2:
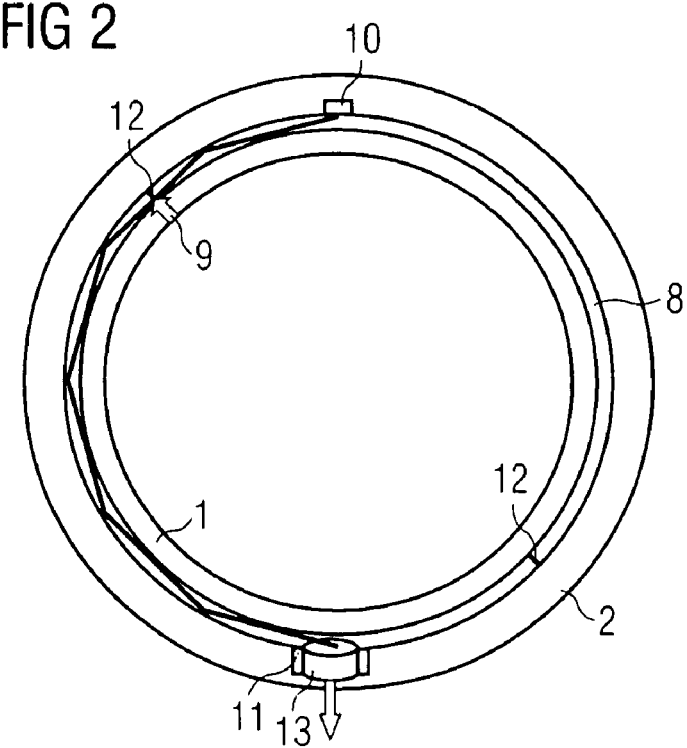
FIG. 2 is a block schematic diagram illustrating the signal path in the channel for an embodiment of the present apparatus.

FIG. 2 shows a first example of the present apparatus for transmitting optical signals between the rotating part 1 and the stationary part 2 of a computer tomograph. Both of the parts are fashioned on their opposing surfaces such that a hollow channel 8 is created that conducts coupled light via internal reflection. Such an embodiment can be learned from U.S. patent Publication 2004/0062344 A1.

For this, at the rotating part 1, laser light 9 is modulated with the measurement data and coupled into the hollow channel 8 in which it propagates in both directions; this is indicated in FIG. 2 by the thick line within the hollow channel 8. At opposite locations of the ring 5 formed by the hollow channel 8, windows are provided on the hollow channel 8, one of which is provided with a light absorber 10 and the other is provided with an exit window 11 for the transmitted light.

Furthermore, at the rotating part 1, two opposing light barriers 12 are likewise arranged on the ring 5 within the hollow channel 8, these light barriers 12 preventing a further propagation of the light in the hollow channel 8. This ensures that respectively only light signals that run in one of the two directions within the hollow channel 8 impinge on the detector. In the present apparatus, at the exit window, an optical concentrator 13 is arranged that is fashioned horn-shaped and that concentrates light exiting from the exit window 11 onto a small detector area of the optical detector (not visible here). The optical concentrator 13 is indicated in this design in only a significantly schematized manner.

Figure 3:
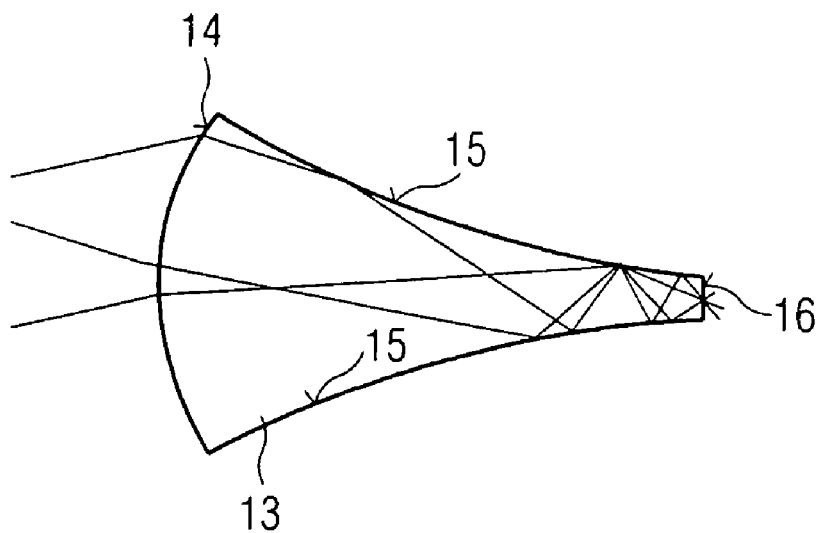
FIG. 3 is a pictorial diagram illustrating an example for the embodiment of the optical concentrator.

FIG. 3 shows a more detailed cross-sectional representation of this optical concentrator 13. The scattered light escaping from the exit window 11 enters into the massive concentrator body via the convexly-fashioned entrance area 14 that is provided with an anti-reflective coating, this concentrator body being formed from an optically transparent material. The side surfaces 15 of the concentrator 13 are provided with a coating highly reflective for the wavelengths of the light used, such that the light radiation incident at different angles is concentrated onto the smaller exit area 16 via multiple reflections within the concentrator 13. In the present example, this exit area 16 is coated with a multi-layer filter that is transparent for the wavelengths used and reflects light of larger wavelengths. The present concentrator 13 therefore acts as a narrowband filter with a central frequency that corresponds to the frequency of the laser light used for signal transmission.

For the dimensioning of the anti-reflection coating on the entrance area 14 of the concentrator 13, the known equation is used:

$$d=(m+1/2)\times\lambda/2\times1/n,$$

where m=0, 1, 2, . . . , d of the thickness of the anti-reflection coating, λ corresponds to the wavelength of the light used for the signal transmission, and n corresponds to the refraction index of the coating material, with 1<n< refraction index of the concentrator material.

For the dimensioning of the highly-reflective coating on the side surfaces of the concentrator 13, the thickness of this coating is calculated with the aid of the following equation:

$$d=m\times\lambda/2\times1/n,$$

whereby m=0, 1, 2, . . . , d of the thickness of the highly-reflective coating, λ corresponds to the wavelength of the light used for the signal transmission, and n corresponds to the refraction index of the coating material, with 1<n< refraction index of the concentrator material.

Figure 4:
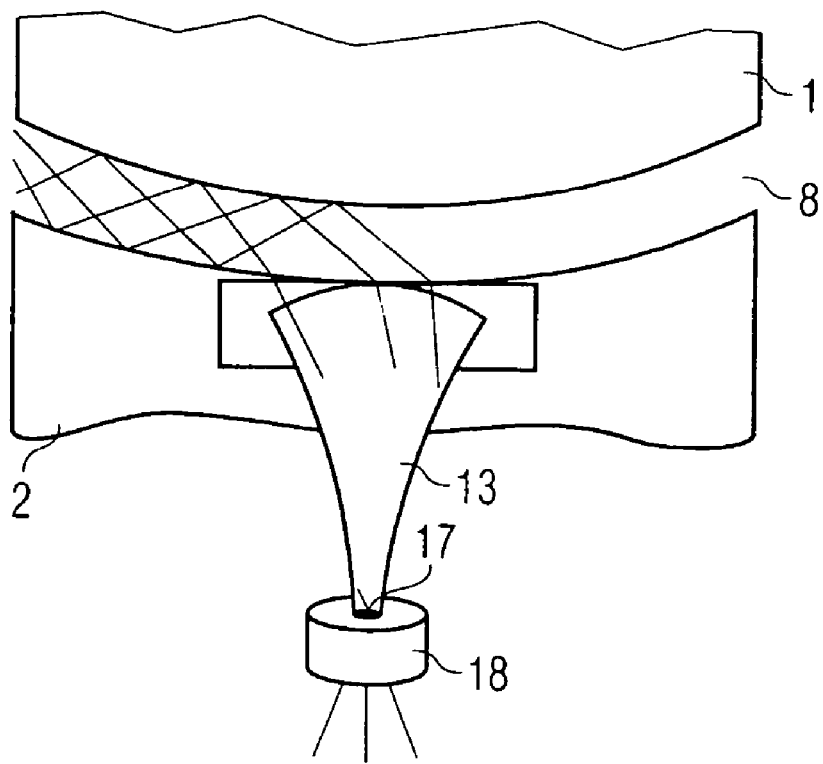
FIG. 4 is a pictorial schematic of a more detailed section from the embodiment according to FIG. 2.

FIG. 4 shows an enlarged section of the apparatus according to FIG. 2, in which the light exiting from the hollow channel 8 via the exit window 11 is indicated. Arranged in the exit opening of the window 11 is the concentrator 13, which captures a large portion of this light and concentrates it onto the small detector area 17 of the detector 18 (in the present example, an APD). A very good signal-to-noise ratio is achieved, via which the bit error rate (BER) in the data transmission is reduced.

Figure 5:
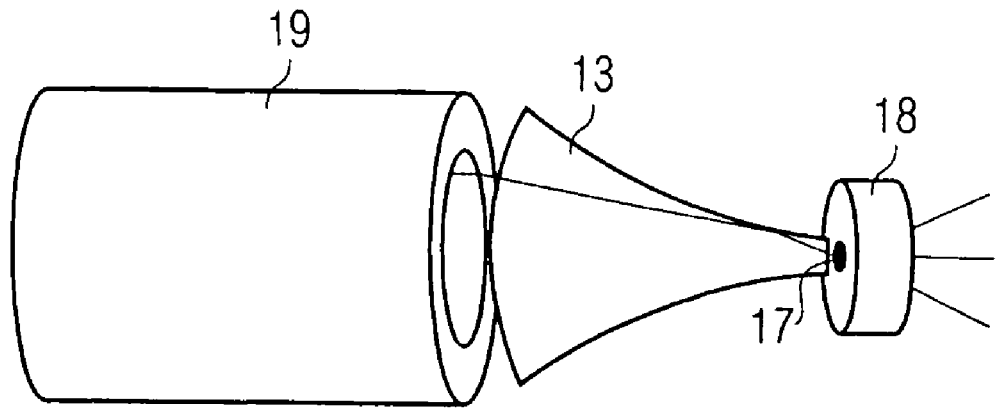
FIG. 5 is an isometric diagram illustrating an example for the arrangement of the optical concentrator given use of a different transmission technique.

In addition to the transmission technique shown in FIG. 2, other transmission techniques can also be used in the present apparatus. FIG. 5 shows an example for a transmission technique in which the light emitted by the transmitter 4 is laterally coupled in a wave guide ring (in the present case an optical fiber 19) attached to the stationary part 2 and is decoupled at an axial end of the fiber 19 onto the detector 18. In this embodiment, of which in FIG. 5 only one end of the fiber 19 with the detector 18 is visible, the optical concentrator 13 is arranged between the end of the fiber 19 and the detector 18. The light, exiting from the fiber with a large core diameter in comparison with the detector area 17, is collected via the concentrator 13 and concentrated onto the small detector area 17. The APD used here also (as in the other examples) has a detector area with a diameter of only, e.g., 0.5 mm or less, such that a high-speed processing is achieved.

Figure 6:
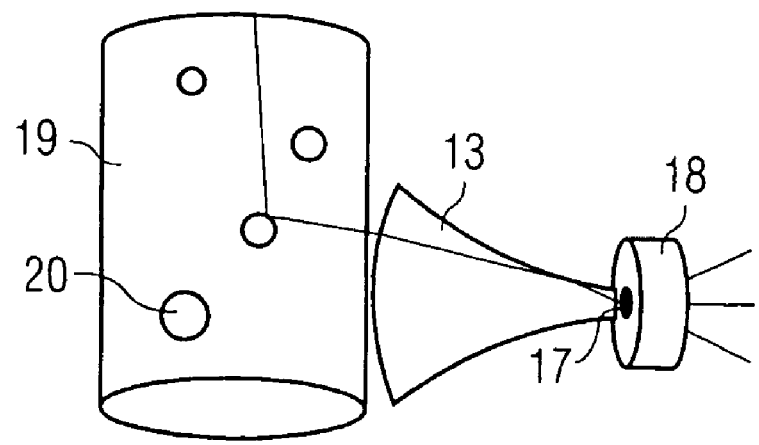
FIG. 6 is an isometric diagram illustrating an example for the arrangement of an optical concentrator given use of a further transmission technique.

FIG. 6 shows a further example in which, at the rotating part 1, a ring made from an optical fiber 19 is used that emits axially coupled light from the transmitter 4 laterally, for example via incorporated scattered bubbles 20 as they are arranged in FIG. 6. The detector 18 arranged on the stationary part 2 thereby respectively acquires only a small region of the optical fibers 19. Via use of the present concentrator 13, the acquisition region can be clearly increased given use of a detector 18 with a small detector area 17 as is necessary for fast processing of the signals.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The particular implementations shown and described herein are illustrative examples of the invention and are not intended to otherwise limit the scope of the invention in any way. For the sake of brevity, conventional electronics and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

| REFERENCE LIST | |
|---|---|
| 1 | rotating part |
| 2 | stationary part |
| 3 | detector bank |
| 4 | transmitter |
| 5 | data transmission ring |
| 6 | receiver |
| 7 | image reconstruction device |
| 8 | hollow channel |
| 9 | laser |
| 10 | light absorber |
| 11 | exit window |
| 12 | light barrier |
| 13 | optical concentrator |
| 14 | entrance area |
| 15 | side surface |
| 16 | exit area |
| 17 | detection area |
| 18 | detector |
| 19 | optical fiber |
| 20 | bubbles |

What is claimed is:

1. An apparatus for transmission of optical signals between a rotating part and a stationary part of a machine, comprising:

an optical transmitter arranged on a first of the two parts;

an optical receiver with an optical detector arranged on a second of the two parts, via which optical signals emitted by the optical transmitter are received, the optical receiver comprising:

an optical concentrator with an at least approximately horn-shaped geometry for concentrating incident optical radiation via internal reflection on side surfaces of the concentrator onto a detection area of the detector, the optical concentrator being formed from a material filling an entire inner volume of the concentrator and optically transparent for at least one wavelength with which the transmitter transmits, the material being capable of being generated via two-photon polymerization.

2. The apparatus according to claim 1, wherein the side surfaces of the concentrator are concavely curved between an entrance are and an exit are of the concentrator.

3. The apparatus according to claim 1, wherein the entrance area of the concentrator is fashioned has a convex shape.

4. The apparatus according to claim 1, wherein the entrance area of the concentrator comprises an anti-reflective coating for the at least one wavelength with which the transmitter transmits.

5. The apparatus according to claim 1, wherein the side surfaces of the concentrator are provided with a coating increasing the internal reflection for the at least one wavelength with which the transmitter transmits.

6. The apparatus according to claim 1, wherein an exit area of the concentrator is provided with a bandpass coating.

7. The apparatus according to claim 1, wherein the optically transparent material is an organically modified ceramic material.

8. The apparatus according to claim 1, wherein the detector is a photodiode with a diameter of the detection area of ≦0.5 mm.

9. The apparatus according to claim 1, wherein the apparatus is fashioned as a computer tomograph.

* * * * *